United States Patent [19]

Renga

[11] Patent Number: 4,612,386

[45] Date of Patent: Sep. 16, 1986

[54] PROCESS FOR MAKING ESTERS

[75] Inventor: James M. Renga, Midland, Mich.

[73] Assignee: The Dow Chemical Company, Midland, Mich.

[21] Appl. No.: 331,704

[22] Filed: Dec. 17, 1981

Related U.S. Application Data

[63] Continuation-in-part of Ser. No. 187,690, Sep. 16, 1980, abandoned.

[51] Int. Cl.$^4$ .................. C07C 67/14; C07D 265/30; C07D 213/803; C07D 213/55; C07D 209/42; C07D 277/62; C07D 277/68; C07D 307/18
[52] U.S. Cl. .................................. 560/86; 544/171; 544/172; 546/263; 546/318; 546/326; 546/327; 546/341; 546/342; 548/156; 548/180; 548/492; 560/81; 560/84; 560/85; 560/95; 560/96; 560/103; 560/109; 560/111; 560/113; 560/127; 560/146; 560/190; 560/193; 560/197; 560/201; 560/204; 560/205; 560/220; 560/221; 560/265; 560/266

[58] Field of Search ....................... 560/81, 84, 85, 86, 560/95, 96, 103, 127, 109, 113, 111, 146, 190, 193, 205, 197, 220, 221, 201, 265, 266, 204; 260/326.46, 347.4, 347.5, 326.13 B, 326.13 C, 326.13 D; 548/201; 546/263, 318, 326, 327, 341, 342; 544/171, 172

[56] References Cited

U.S. PATENT DOCUMENTS

| | | | |
|---|---|---|---|
| 3,148,207 | 9/1964 | Weinkauff et al. | 560/204 |
| 3,256,305 | 6/1966 | Gizen | 560/84 |
| 3,326,958 | 1/1967 | Curtius et al. | 560/103 |

FOREIGN PATENT DOCUMENTS 13663  7/1980  European Pat. Off. .

OTHER PUBLICATIONS

Ishido, Carbohydrate Research, 52, (1976), pp. 49–61.

Primary Examiner—Natalie Trousof
Assistant Examiner—Vera C. Clarke

[57] ABSTRACT

Carboxylic acid esters are produced by the reaction of a carboxylic acid halide with a carbonate ester in the presence of an initiator. The reaction of a dicarboxylic acid dihalide and a bis(alkyl carbonate) ester produces a polymeric polyester.

15 Claims, No Drawings

PROCESS FOR MAKING ESTERS

CROSS-REFERENCE TO RELATED APPLICATION

This is a continuation-in-part of my copending application Ser. No. 187,690, filed Sept. 16, 1980, now abandoned.

BACKGROUND OF THE INVENTION

This invention relates to a new chemical process for making esters of carboxylic acids. The process includes the preparation of commercially useful polyester plastics.

The esterification of alcohols with carboxylic acids is typically carried out in the presence of acidic catalysts. This reaction is reversible and a major problem is finding a method of displacing the reaction equilibrium so as to obtain a high conversion to the ester. This is often accomplished by removing water and/or ester by distillation as the reaction proceeds.

Acid chlorides and acid anhydrides react more readily with alcohols than the carboxylic acids themselves and require much milder reaction conditions. These reactions are irreversible, but they produce coproduct acids which must be removed from the reaction mixture or neutralized.

Transesterification, the reaction of the ester of one alcohol with a second alcohol to make the ester of the second alcohol plus the free first alcohol by an ester interchange or alcoholysis reaction is well-known. This reaction can usually be run with either acidic or basic catalysis.

Organic carbonates, the diesters of carbonic acid, can be prepared by reactions analogous to those listed above for carboxylic acids generally. A commonly used procedure for making carbonates is the reaction of an alcohol with phosgene, the acid chloride of carbonic acid, in the presence of an acid acceptor. Polycarbonates are produced in this way, e.g., the condensation of bisphenol A with phosgene in the presence of pyridine.

All of these conventional esterification methods involve various disadvantages including the use of acidic or basic catalysts, the production of acidic coproducts, and the use of an acid acceptor as well as the need for special product separation and purification procedures associated with such methods.

It is known that cyclic carbonates react with carboxylic acid halides to produce corresponding haloalkyl esters of the carboxylic acid with the elimination of carbon dioxide (see VanGijzen, U.S. Pat. No. 3,256,305). The process is limited to the reaction of certain cyclic carbonates and the production of a particular class of substituted esters.

SUMMARY OF THE INVENTION

It has now been found that a carbonate ester of the formula $R(OCO_2R')_m$ reacts with a carboxylic acid halide of the formula $R''(COX)_n$ in the presence of an initiator compound to produce a high yield of the corresponding carboxylic acid ester with elimination of the volatile halide $R'X$ and $CO_2$ as coproducts of the reaction according to the equation:

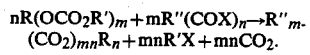

In the above formulas, m and n are each an integer of from 1 to 3 corresponding to the valence of groups R and R" respectively, R is any monovalent, divalent or trivalent aliphatic, cycloaliphatic, aromatic, or heterocyclic radical, saturated or unsaturated, polymeric or monomeric and unsubstituted or substituted with one or more groups unreactive in the process, R' is a group of up to 4 carbons selected from the group consisting of alkyl, alkenyl and inertly-substituted derivatives thereof, R" is any monovalent, divalent or trivalent radical as defined for R with the addition of corresponding oxy radicals, e.g., alkoxy, aryloxy, and the like and X or XC(O)—, and X is Cl, Br, or I. In addition $R(CO_2R')_m$ and $R''(COX)_n$ jointly may define a single structure having both ester and carboxylic acid halide functionality in the same molecule, that is a compound on which R and R" are covalently bonded to each other.

DETAILED DESCRIPTION OF THE INVENTION

Depending upon the values of m and n in the above formulas, the reaction produces a monoester, a diester, a triester, or a polymeric ester structure. For example, when m and n are both two, the product is a polyester where the molecular structure consists essentially of repeating units of the formula $\{R-OOC-R'-COO\}$, the formula $R''_m(CO_2)_{mn}R_n$ in this case representing an empirical equivalent of that structure. Since R" can also be an oxy radical as noted, the ester or polyester product can be a carbonate or polycarbonate as well as other carboxylic acid ester or polyester.

In the above formulas and equation, R can be a monovalent group such as methyl, butyl, tert-octyl, dodecyl, hexadecyl, vinyl, allyl, methylbutenyl, octenyl, octadecenyl, cyclopentyl, cyclohexyl, cyclohexenyl, tetrahydrofuryl, pyridyl, indolyl, morpholinyl, benzothiazolyl, phenyl, naphthyl, benzyl, or phenethyl, or any of these having up to about three substituents unreactive in the process. Such substituents include lower alkyl, lower alkoxy, halo, nitro, ester groups, trifluoromethyl, aralkyl, phenyl, and phenoxy. When R is divalent or trivalent, it represents a group corresponding to one of those such as cited above, e.g., trimethylene, dodecylene, cyclohexylene, phenylene, alkylidenediphenylene, benzylidene, alkylidynetriphenylene, oxydiphenylene, and the like.

R' represents a lower alkyl radical, lower alkenyl radical or inertly-substituted derivative thereof such as methyl, ethyl, isopropyl, butyl, allyl, or halogenated derivatives thereof. Preferably R' is a lower alkyl. Most preferably R' is a methyl group. X is preferably Br or Cl, most preferably Cl. The reaction proceeds with elimination of $CO_2$ and the volatile halide R'X from the reaction mixture. Consequently, when R'X is the highly volatile methyl chloride, the reaction is particularly accelerated and separation of the ester product is also thereby facilitated.

The groups represented by R" are also monovalent, divalent, or trivalent groups such as those represented by R plus corresponding oxy radicals, for example, butoxy, allyloxy, tetramethylenedioxy, a glycerol residue, phenoxy, phenylenedioxy, benzyloxy, cyclohexanedioxy, pyridoxy, and the like, with or without inert substituents as listed above, and X or XC(O)—. Examples of the latter class include phosgene or oxalyl chloride.

As mentioned above, the reactants may be polymeric as, for example, where the carbonate ester is an alkyl ester of a polymeric carbonate compound. An example would be the methyl ester of oligomeric bisphenol A dicarbonate.

Although the process can be operated at any temperature in the broad range of about 25° C.–250° C., it is preferably carried out at about 50° C.–250° C. and most preferably 100° C.–175° C. for most convenient operation conditions and reaction time. The reaction time can vary from about 0.1 hour to about 10 hours depending upon the reaction conditions.

A reaction solvent is usually not required or desirable, but use of a solvent may be advantageous under some conditions, e.g., when low boiling reactants are employed. Polar solvents appear to increase the rate of reaction. Relatively high boiling inert solvents such as N,N-dimethylformamide, sulfolane, glycol diethers, and substituted aromatics such as anisole, o-dichlorobenzene, alkylated pyridines, and the like are preferred.

Initiator compounds that are suitably employed in the process include those compounds that act as catalysts in the process and also those compounds that themselves may not possess catalytic properties but are capable of forming catalysts in situ. Catalysts include acids, bases and salts. Examples of acid catalysts include mineral acids, organic acids and solid acids such as Lewis acids, and acidic ion-exchange materials such as natural or artificial zeolites or organic ion-exchange resins. Basic catalysts include both organic and inorganic bases and basic ion-exchange materials. Salts include metal salts of acids such as metal halides, sulfate or bicarbonates and quaternary salts such as ammonium, sulfonium, sulfoxonium or phosphonium salts. Other suitable initiators are those compounds capable of forming in situ one or more of the above catalysts. Examples of the latter include amine or phosphine compounds capable of reaction with further components of the reaction mixture, e.g, organic halogen compounds, to form ammonium or phosphonium salts.

More particularly, acid catalysts include sulfuric acid, hydrochloric acid, toluene sulfonic acid, potassium bisulfate, zinc chloride, aluminum chloride, and acid-exchanged resins of chlorinated (poly)styrene cross-linked with divinylbenzene or similar cross-linking substance. Basic compounds include amines such as pyridine or triethylamine, and alkali metal hydroxides or carbonates. Salts include inorganic sulfate, nitrate, phosphate or halide salts, or organic formate, acetate, benzoate, phenate or bisphenate salts of alkali metals, alkaline earth metals, metals of groups Ib, IIb and VIII of the Periodic Table and ammonium, sulfonium, sulfoxonium or phosphonium quaternary ions. The latter class of ammonium or phosphonium quaternary ions are additionally described as follows.

Preferably, these salts have the general formula $(R''')_4AY$ where each $R'''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate as previously described. The $R'''$ groups may be alkyl, aryl, alkaryl, aralkyl, or cycloalkyl. Also, two $R'''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above.

Also, amine and phosphine salts such as tributylamine hydrochloride which are a form of quaternary salt will catalyze the reaction although these are generally less desirable in the reaction mixture. Additionally, it is possible to form the quaternary salt in situ. For example, when a nitrogen-containing solvent such as N,N-dimethylformamide or N,N-dimethylacetamide is employed in the process, the small amount of quaternary salt formed by interaction of the amide nitrogen atom with the halide reactant (or alkyl halide product) is sufficient to catalyze the reaction. The same is true of a small amount of amine or phosphine compound is added to the reaction mixture to form such quaternary salt.

Although any significant amount of the previously identified initiator compound will catalyze the reaction to some extent, for practical reasons in batch operations, it is preferred to use about 0.1–10 mole percent of the initiator based on the carbonate. More initiator can be used but the excess confers little added advantage and may in fact be disadvantageous. The preferred initiators are ammonium or phosphonium salts that allow the reaction process to be conducted under relatively neutral reaction conditions.

In a mode of the invention particularly adapted to continuous operation, one or more $R'''$ groups may be pendant methylene groups from a resin matrix so that the quaternary salt is a salt form of a strong base anion-exchange resin such as DOWEX ® 21K, DOWEX ® 11, DOWEX ® MWA-1, or other such commercially available ion-exchange resins or the phosphonium equivalents of such quaternary ammonium-substituted resins. In such a continuous operation of the process, the mixed reactants are passed at an appropriate flow rate through a bed of the strong base anion resin maintained at a suitable temperature within the limits previously defined.

Batchwise operation of the process involves simply combining the reactants and initiator and heating until the evolution of carbon dioxide and alkyl halide has ceased.

The process is ordinarily carried out at atmospheric pressure but it may be carried out at somewhat reduced pressure to hasten the removal by distillation of the volatile alkyl halide product. Passage of a stream of nitrogen or other inert gas through or over the reaction mixture may also be beneficial in this respect for some mixtures.

This process provides the advantages of a moderate temperature and ready separation of the ester product as well as the organic halide coproduct. In addition, when the quaternary salt initiators of the invention are employed, substantial neutral reaction conditions are obtained. The volatile reaction products are carbon dioxide which can simply be vented and the organic halide which can be recovered by condensation or adsorption. The residue in the reaction vessel is primarily the desired ester together with the small amount of the initiator and, in some cases, a minor amount of the alkyl phenyl ether produced by the decomposition of the carbonate reactant. The desired ester product is readily recovered and purified by conventional means such as distillation or recrystallization depending on its physical properties.

The carbonate starting material can be made by any of several known methods for making these esters. A common preparatory method is the reaction of an alcohol or phenol with an alkyl chloroformate under basic conditions. Unsymmetrical carbonates can also be made by the acid or base catalyzed reaction of an alcohol or phenol with a symmetrical carbonate ester, for example, the reaction of phenol with dimethyl carbonate to make methyl phenyl carbonate and the corresponding reaction of a pyridinol to make the methyl pyridyl carbonate.

EXAMPLE 1

A mixture of 7.03 g (0.05 g mole) of benzoyl chloride, 4.5 g (0.05 g mole) of dimethyl carbonate, and 0.85 g (0.0025 g mole) of tetra-n-butyl phosphonium bromide (TBPB) in 25 ml of sulfolane was heated at 150° C. in a reaction flask equipped with reflux condenser. After 22 hours, the condenser was replaced by a distillation head and 6.3 g (93 percent yield) of methyl benzoate distilled at 83° C.-85° C./17 mm.

EXAMPLE 2

A mixture of the same molar amounts used in Example 1 of trimethylacetyl chloride, dimethyl carbonate, and TBPB in 25 ml of sulfolane was heated 18 hours at 125° C. as described above. An 84 percent yield of methyl trimethylacetate was obtained by distillation of the reaction mixture.

EXAMPLE 3

The procedure of Examples 1 and 2 was repeated to react acetyl chloride with dimethyl carbonate in sulfolane with TBPB present to produce a distilled yield of about 35-40 percent of methyl acetate. The reaction mixture was heated 20 hours at 115° C.

EXAMPLE 4

A mixture of 7.03 g of benzoyl chloride, 7.61 g of methyl phenyl carbonate, and 0.17 g of TBPB was heated for 2 hours at 150° C. to give 100 percent conversion of the carbonate to phenyl benzoate. A 97 percent yield of purified phenyl benzoate, b.p. 131°-2° C./3 mm was obtained by vacuum distillation of the reaction mixture.

EXAMPLE 5

When the procedure of Example 4 was repeated using 9.25 g of benzoyl bromide instead of the chloride and the reaction mixture was heated one hour at 150° C., 99 percent of the carbonate was converted to phenyl benzoate. A 94 percent yield of purified phenyl benzoate was obtained by vacuum distillation.

EXAMPLE 6

A mixture of 1.75 g of p-chlorobenzoyl chloride, 1.82 g of methyl p-methoxyphenyl carbonate, and 0.034 g of TBPB was heated for 4 hours at 150° C. to produce 100 percent conversion of the carbonate to p-methoxyphenyl p-chlorobenzoate. Recrystallization of the crude product from ether gave 2.1 g (80 percent yield) of the purified ester, m.p. 101°-2° C.

EXAMPLE 7

A mixture of 2.81 g (0.02 mole) of benzoyl chloride, 3.44 g (0.01 mole) of bisphenol A bis(methyl carbonate), and 0.068 g of TBPB was heated at 150° C. for 2 hours to give a quantitative yield of bisphenol A dibenzoate, m.p. 157° C.-159° C.

EXAMPLE 8

Example 7 was repeated using 0.07 g of tetra-n-butyl ammonium iodide as the catalyst. After 3 hours at 150° C., 91 percent of the dicarbonate had been converted to bisphenol A dibenzoate.

EXAMPLE 9

A mixture of 7.73 g of p-toluyl chloride, 5.91 g of diethyl carbonate, and 0.85 g of TBPB in 25 ml of sulfolane was heated at 170° C. under reflux. After 44 hours, the reaction mixture was added to 200 g of crushed ice and this was extracted twice with 25-ml portions of hexane. The combined extracts were dried over anhydrous $Na_2SO_4$ and distilled to obtain 6.4 g (78 percent yield) of ethyl p-toluate, b.p. 120°-1° C./20 mm.

EXAMPLE 10

A mixture of 7.83 g (0.05 mole) of phenyl chloroformate, 7.61 g (0.05 mole) of methyl phenyl carbonate, and 0.17 g of TBPB was heated for one hour at 150° C. Essentially all of the methyl phenyl carbonate was converted to diphenyl carbonate. Distillation of the reaction mixture gave 10.45 g (98 percent yield) of diphenyl carbonate, b.p. 138° C./3 mm.

EXAMPLE 11

A mixture of 7.83 g (0.05 mole) of phenyl chloroformate, 2.48 g (0.0275 mole) of dimethyl carbonate, and 0.85 g of TBPB was heated at 150° C. under a reflux condenser for 4 hours when all gas evolution had ceased. Distillation of the reaction mixture gave 5.25 g (98 percent yield based on chloroformate) of diphenyl carbonate.

EXAMPLE 12

A mixture of 6.26 g (0.04 mole) of phenyl chloroformate, 6.88 g (0.02 mole) of bisphenol A bis(methyl carbonate), and 0.14 g of TBPB was heated at 120° C. for 15 minutes, then at 150° C. for 30 minutes to convert all of the carbonate starting material to bisphenol A bis(phenyl carbonate).

EXAMPLE 13

Methyl 3,5,6-trichloro-2-pyridyl carbonate was prepared by reacting methyl chloroformate with 3,5,6-trichloro-2-pyridinol at 0° C.-5° C. in the presence of an equivalent of pyridine as acid acceptor and using methylene chloride as the reaction solvent.

A mixture of 6.41 g (0.025 mole) of methyl 3,5,6-trichloro-2-pyridyl carbonate, 3.51 g (0.025 mole) of benzoyl chloride, and 0.034 g (0.0001 mole) of tetra-n-butyl phosphonium bromide was heated in a reaction flask at 125° C. for 1.5 hours to produce greater than 99 percent conversion of the carbonate to 3,5,6-trichloro-2-pyridyl benzoate. Recrystallization of the product from ether gave 6.35 g (84 percent yield) of purified benzoate, m.p. 101°-2° C.

EXAMPLE 14

A mixture of 6.887 g (0.02 mole) of bisphenol A bis(methyl carbonate), 2.07 g of isophthalyl chloride, 2.07 g of terephthalyl chloride (0.0204 g mole total acid dichlorides), 0.14 g of tetra-n-butylphosphonium chloride, and 25 ml of o-dichlorobenzene was heated at 180°

C.-185° C. for 4 hours in a resin pot with vigorous mechanical stirring. The viscous liquid reaction mixture was then removed from the resin pot and the solvent was removed by evaporation at 100° C. under reduced pressure. The residue amounted to 8.25 g of an opaque solid polymer which was essentially a linear isopropylidene diphenylene phthalate polyester wherein the phthalate moieties were randomly mixed terephthalate and isophthalate groups. This material had an inherent viscosity ($\eta_{inh}$) at 25° C. in methylene chloride of 0.39 dl/g which corresponds to an average molecular weight of about 33,000. The crude polyester was dissolved in 200 ml of methylene chloride and was washed successively with 10 ml of 5 percent aqueous NaHCO$_3$ and 10 ml of saturated aqueous NaCl, then was dried over anhydride MgSO$_4$. The polyester was then precipitated by adding 600 ml of hexane and residual solvent wa removed from the filtered precipitate by evaporation under vacuum. The purified polyester was a colorless solid having an inherent viscosity at 25° C. in methylene chloride of 0.62 dl/g corresponding to an average molecular weight of about 52,000. The purified polyester melted at 261° C.-262° C.

EXAMPLE 15

The procedure of Example 14 was repeated except for using 25 ml of anisole in place of the o-dichlorobenzene and heating the reaction mixture for 4 hours at 150° C.-155° C. The crude polyester obtained after solvent removal had an inherent viscosity of 0.16 dl/g determined at 25° C. in methylene chloride. This corresponds to a molecular weight of about 14,000. The polyester was otherwise similar to the polyester product of Example 14.

EXAMPLE 16

This example illustrates the use of initiator compounds capable of in situ formation of catalysts, e.g., quaternary ammonium salts. The example additionally illustrates the formation of haloalkyl-substituted esters where the carbonate reactant is initially halogenated.

A mixture of 9.35 g (0.05 mole) of bis(2-chloroethyl)-carbonate, 7.03 g (0.05 mole) of benzoyl chloride and 0.655 g (0.0025 mole) of triphenylphosphine was heated to 180° C. in a reaction flask equipped with a distillation head. After 2 hours, 1.6 g (92 percent yield) of 1,2-dichloroethane had collected. Further distillation gave 8.15 g (88 percent yield) of 2-chloroethyl benzoate, b.p. 81° C.-82° C./0.4 mm Hg.

EXAMPLE 17

The reaction procedure of Example 16 was repeated using 0.85 g (0.0025 mole) of tetra-n-butylphosphonium bromide as the catalyst. 2-Chloroethyl benzoate (6.9 g, 75 percent yield) was isolated, b.p. 81° C.-82° C./0.4 mm Hg.

EXAMPLE 18

A mixture of 6.93 g (0.05 mole) of 2-chloroethyl methyl carbonate, 7.03 g (0.05 mole) of benzoyl chloride and 0.85 g (0.0025 mole) of tetra-n-butylphosphonium bromide was heated to 150° C. After 3 hours, gas evolution had ceased and distillation gave 5.44 g (59 percent yield) of 2-chloroethyl benzoate at b.p. 81° C.-82° C./0.4 mm Hg.

EXAMPLE 19

The following example illustrates the use of reactants wherein R' is allyl and the catalyst is a Lewis acid.

In a glass reactor benzoyl chloride (7.03 g, 0.05 mole), diallyl carbonate (7.1 g, 0.05 mole) and zinc chloride (0.136 g, 0.001 mole) were combined. The reacinitiated at room temperature. After heating at 60° C. for 3 hours and heating at 80° C. for an additional 3 hours, the reaction was discontinued. Distillation gave 6.65 g (78 percent yield) of allyl benzoate which was identified by nuclear magnetic resonance spectroscopy.

EXAMPLE 20

The following example illustrates the use of alkali halide catalysts. A mixture of benzoyl chloride (7.03 g, 0.05 mole), dimethyl carbonate (4.5 g, 0.05 mole) and lithium chloride (0.106 g, 0.0025 mole) in 25 ml of sulfolane was heated to 150° C. for 22 hours. Distillation of the reaction mixture gave 4.77 g (70 percent yield) methyl benzoate.

EXAMPLE 21

The following example illustrates the use of basic amine catalysts. A mixture of benzoyl chloride (7.03 g, 0.05 mole), diallyl carbonate (7.10 g, 0.05 mole) and N,N-dimethylaminopyridine (0.06 g) were combined in a glass reaction vessel and heated to 170° C. for 4 hours. Distillation of the reaction mixture gave allyl benzoate, b.p. 110° C.-111° C. (13 mm Hg). Yield was 90 percent.

In the same way as described and illustrated above, other monoesters, diesters, and polymeric polyesters are prepared using the appropriate carbonate and acyl halide reactants.

I claim:

1. A process for making an ester having the formula $R''_m(CO_2)_{mn}R_n$ which comprises contacting a carbonate ester of the formula $R(OCO_2R')_m$ with a carboxylic acid halide of the formula $R''(COX)_n$, wherein R singly is an aliphatic, cycloaliphatic, aromatic, or heterocyclic group having a valence of m, R" singly is a group as defined by R, X, XC(O)—or $RO_n$ and has a valence of n, and R and R" jointly may be covalently bonded together, R' is a group of up to 4 carbons selected from the group consisting of alkyl, alkenyl, and halogenated derivatives thereof, m and n are each an integer from one to three, and X is Cl, Br, or I, in the presence of a catalytic amount of an acid selected from the group consisting of mineral acids, organic acids, Lewis acids and acidic ion-exchange materials; a base selected from the group consisting of amines, alkali metal hydroxides, and alkali metal carbonates; a salt selected from the group consisting of sulfate, nitrate, phosphate, halide, formate, acetate, benzoate, phenate and bisphenate salts of alkali metals, alkaline earth metals, metals of Groups Ib, IIb or VIII of the Periodic Table and ammonium, sulfonium, sulfoxonium or phosphonium quaternary ions or a compound capable of forming in situ a catalytic amount of an above-defined acid, base or salt at about 25° C.-250° C.

2. The process of claim 1 wherein the initiator compound is an acid selected from the group consisting of the group consisting of mineral acids, organic acids, Lewis acids and acidic ion-exchange materials; a base selected from amines, alkali metal hydroxides, and alkali metal carbonates; or a salt selected from the group consisting of sulfate, nitrate, phosphate, halide, formate, acetate, benzoate, phenate and bisphenate salts of alkali metals, alkaline earth metals, metals of Groups Ib, IIb or VIII of the Periodic Table and ammonium, sulfonium, sulfoxonium or phosphonium quaternary ions.

3. The process of claim 1 wherein R' is lower alkyl.

4. The process of claim 1 wherein R' is a methyl group.

5. The process of claim 1 which comprises contacting a lower alkyl carbonate of the formula $R(OCO_2R')_m$ with a carboxylic acid halide of the formula $R''(COX)_n$, wherein R is an aliphatic, cycloaliphatic, aromatic, or heterocyclic group having a valence of m, R' is a lower alkyl group, R" is a group as defined by R or $RO_n$ and has a valence of n, m and n are each an integer from one to three, and X is Cl, Br, or I, in the presence of a quaternary ammonium or phosphonium salt at about 50° C.–250° C.

6. The process of claim 1 wherein m and n are each one.

7. The process of claim 6 wherein R is a polychloropyridyl group.

8. The process of claim 6 wherein R is a phenyl group.

9. The process of claim 1 wherein X is Cl.

10. The process of claim 1 wherein the temperature is about 100° C.–175° C.

11. The process of claim 1 wherein m is two and n is one.

12. The process of claim 11 wherein R is an isopropylidenediphenylene group.

13. The process of claim 1 wherein m and n are both two and the ester product is a polymeric polyester.

14. The process of claim 13 wherein R is an isopropylidenediphenylene group and R" is a phenylene group.

15. The process of claim 14 wherein the formula $R(OCO_2R')_2$ represents bisphenol A bis(methyl carbonate) and the formula $R''(COX)_2$ represents a mixture of isophthalyl chloride and terephthalyl chloride.

* * * * *